(12) United States Patent
Moriwaki et al.

(10) Patent No.: US 6,589,949 B1
(45) Date of Patent: Jul. 8, 2003

(54) 3-OXO-2,1-BENZISOXAZOL-1(3H)-CARBOXAMIDES FOR TREATMENT OF CNS DISEASES

(75) Inventors: Toshiya Moriwaki, Nara (JP); Chantal Fürstner, Mühlheim (DE); Bernd Riedl, Wuppertal (DE); Jens-Kerim Ergüden, Wülfrath (DE); Frank Böss, Wuppertal (DE); Bernard Schmidt, Lindlard (DE); Franz-Josef van der Staay, Lohmar (DE); Werner Schröder, Wuppertal (DE); Karl-Heinz Schlemmer, Wuppertal (DE); Nagahiro Yoshida, Kyoto (JP)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/149,658

(22) PCT Filed: Dec. 6, 2000

(86) PCT No.: PCT/EP00/12268

§ 371 (c)(1),
(2), (4) Date: Oct. 22, 2002

(87) PCT Pub. No.: WO01/44211

PCT Pub. Date: Jun. 21, 2001

(30) Foreign Application Priority Data

Dec. 17, 1999 (DE) .......................... 199 60 917

(51) Int. Cl.⁷ .................. A61K 31/5377; A61P 25/28; C07D 261/20; C07D 41/306
(52) U.S. Cl. .................. 514/233.8; 544/137; 548/241
(58) Field of Search .......... 544/137; 548/241; 514/233.8

(56) References Cited

FOREIGN PATENT DOCUMENTS

WO 9602537 1/1996

OTHER PUBLICATIONS

Stoffel, et al, *Chemical Abstracts*, vol. 79, No. 137075, 1973.*

* cited by examiner

*Primary Examiner*—Robert W. Ramsuer
(74) *Attorney, Agent, or Firm*—Susan M. Pellegrino

(57) ABSTRACT

The invention relates to novel 3-oxo-2,1-benzisomazol-1 (3H)-carboxamides (I), where $R^1$, $R^2$ are the same or different and independently=H, halogen, $C_1$ $C_6$ alkyl $C_1$ $C_6$ alkoxy, $C_1$ $C_3$ perfluoroalkyl, or a group $NR^5R^6$; $R^3$, $R^4$ are the same or different and independently=$C_1$ $C_8$ alkyl, whose carbon chain is optionally interrupted by an O, S or $NR^7$ and is optionally singly or severally substituted by $C_3$ $C_6$ cycloalkyl, $C_1$ $C_4$ alkoxy, OH, halogen or $NR^8R^9$; $C_3$ $C_8$ cycloalkyl whose carbon chain is optionally interrupted by an O, S or $NR^{10}$ and is optionally singly or severally substituted by $C_1$ $C_4$ alkoxy, OH, halogen or $NR^{11}R^{12}$, or $R^3$ and $R^4$ together with a nitrogen atom form a saturated or partially unsaturated 3- to 10-membered mono- or bi-cyclic heteocycle, which, optionally, contains up to two further heteroatoms, from N, O or S and is, optionally, substituted by $C_1$ $C_4$ alkyl, $C_1$ $C_4$ alkoxy, OH, halogen, $COOR^{13}$ or $NR^{14}R^{15}$ and X=O or S. The invention further relates to methods for production thereof and use thereof in the production of medicaments for the prophylaxis and/or treatment of diseases of the central nervous system, in particular, cognitive disorders, such as Alzheimer's disease and other forms of dementia, cerebral infarct, skull and brain trauma and pain.

10 Claims, No Drawings

3-OXO-2,1-BENZISOXAZOL-1(3H)-CARBOXAMIDES FOR TREATMENT OF CNS DISEASES

The present invention relates to new 3-oxo-2,1-benzisoxazole-1(3H)-carboxamides, processes for their preparation and their use for the production of medicaments for the prophylaxis and/or treatment of disorders of the central nervous system, in particular cognitive disorders such as Alzheimer's disease and other forms of dementia, cerebral infarct, craniocerebral trauma and pain.

Acylpeptide hydrolase (ACPH) is a serine protease which cleaves N-acetylated amino acids of peptides. A function of ACPH is the degradation of N-acetylated hormones and neuropeptides. ACPH is inhibited by low concentrations of diisopropyl fluorophosphate (DFP) (WO-A-99/52516). Investigations in the 'Morris test', an animal model of learning and memory, showed that DFP has a promoting action on learning and memory processes (*J. Pharmacol. Exp. Ther.* 1996, 278, 697–708). The use of ACPH inhibitors for the treatment of Alzheimer's disease and for improving the cognitive power has been described beforehand (WO-A-99/52516).

WO-A-96/02537 discloses benzo-fused 5-membered heterocyclyl-carboxamides for the treatment of disorders of the central nervous system.

The synthesis and the antimicrobial and antileukemic action of 1-(1-mono-alkylamino-carbonyl)-2,1-benzisoxazol-3(1H)-ones has been described (*J. Med. Chem.* 1984,27, 1212–1215).

The present invention relates to compounds of the general formula (I),

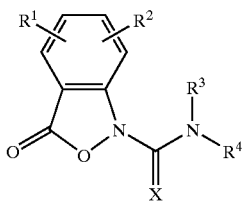

(I)

in which
R$^1$ and R$^2$ are identical or different and independently of one another
represent hydrogen, halogen, (C$_1$–C$_6$)-alkyl, (C$_1$–C$_6$)-alkoxy, (C$_1$–C$_3$)-perfluoroalkyl, (C$_1$–C$_3$)-perfluoroalkoxy or a radical-NR$^5$R$^6$,
in which
R$^5$ and R$^6$ are identical or different and represent hydrogen, (C$_1$–C$_4$)-alkyl, (C$_1$–C$_4$)-acyl, (C$_1$–C$_4$)-alkoxycarbonyl, carbamoyl, mono- or di-(C$_1$–C$_4$)-alkylaminocarbonyl,
R$^3$ and R$^4$ are identical or different and independently of one another
represent (C$_1$–C$_8$)-alkyl whose carbon chain is optionally interrupted by an oxygen or sulfur atom or by a radical NR$^7$ and which is optionally mono- or polysubstituted by radicals selected from the group consisting of (C$_3$–C$_6$)-cycloalkyl, (C$_1$–C$_4$)-alkoxy, hydroxyl, halogen or NR$^8$R$^9$,
represent (C$_3$–C$_8$)-cycloalkyl whose carbon chain is optionally interrupted by an oxygen or sulfur atom or by a radical NR$^{10}$ and which is optionally mono- or polysubstituted by radicals selected from the group consisting of (C$_1$–C$_4$)-alkoxy, hydroxyl, halogen or NR$^{11}$R$^{12}$, in which
R$^7$, R$^8$, R$^9$, R$^{10}$, R$^{11}$ and R$^{12}$ are identical or different and independently of one another have the meaning mentioned for R$^5$,
or
R$^3$ and R$^4$, together with the nitrogen atom, form a saturated or partially unsaturated 3- to 10-membered, mono- or bicyclic heterocycle, which optionally contains up to two further heteroatoms selected from the group consisting of nitrogen, oxygen or sulfur, and which is optionally substituted by radicals selected from the group consisting of (C$_1$–C$_4$)-alkyl, (C$_1$–C$_4$)-alkoxy, hydroxyl, halogen, COOR$^{13}$ or NR$^{14}$R$^{15}$,
in which
R$^{13}$ denotes hydrogen or (C$_1$–C$_4$)-alkyl, and
R$^{14}$ and R$^{15}$ are identical or different and independently of one another have the meaning mentioned for R$^5$,
and
X represents oxygen or sulfur,
and their salts.

Halogen in the context of the invention in general represents fluorine, chlorine, bromine and iodine. Fluorine, chlorine and bromine are preferred. Fluorine and chlorine are particularly preferred.

(C$_1$–C$_6$)-alkyl or (C$_1$–C$_4$)-alkyl in the context of the invention represent a straight-chain or branched alkyl radical having 1 to 6 or 1 to 4 carbon atoms. Examples which may be mentioned are: methyl, ethyl, n-propyl, isopropyl, tert-butyl, n-pentyl and n-hexyl. A straight-chain or branched alkyl radical having 1 to 4 carbon atoms is preferred. A straight-chain or branched alkyl radical having 1 to 3 carbon atoms is particularly preferred.

(C$_1$–C$_6$)-alkoxy in the context of the invention represents a straight-chain or branched alkoxy radical having 1 to 6 carbon atoms. Examples which may be mentioned are: methoxy, ethoxy, n-propoxy, isopropoxy, tert-butoxy, n-pentoxy and n-hexoxy. A straight-chain or branched alkoxy radical having 1 to 4 carbon atoms is preferred. A straight-chain or branched alkoxy radical having 1 to 3 carbon atoms is particularly preferred.

(C$_1$–C$_3$)-perfluoroalkyl in the context of the invention represents a perfluorinated straight-chain or branched alkyl radical having 1 to 3 carbon atoms. Examples which may be mentioned are: trifluoromethyl, pentafluoroethyl and heptafluoroisopropyl. Trifluoromethyl is preferred.

(C$_1$–C$_3$)-perfluoroalkoxy in the context of the invention represents a perfluorinated straight-chain or branched alkoxy radical having 1 to 3 carbon atoms. Examples which may be mentioned are: trifluoromethoxy, pentafluoroethoxy and heptafluoroisopropoxy. Trifluoromethoxy is preferred.

(C$_1$–C$_4$)-acyl or (C$_1$–C$_3$)-acyl in the context of the invention represents a straight-chain or branched acyl radical having 1 to 4 or 1 to 3 carbon atoms. Examples which may be mentioned are: formyl, acetyl, propionyl, n-butyryl and iso-butyryl. Formyl, acetyl and propionyl are preferred.

(C$_1$–C$_4$)-alkoxycarbonyl in the context of the invention represents a straight-chain or branched alkoxycarbonyl radical having 1 to 4 carbon atoms. Examples which may be mentioned are: methoxycarbonyl, ethoxycarbonyl, n-propoxycarbonyl, isopropoxycarbonyl and tert-butoxycarbonyl.

Mono- or di-(C$_1$–C$_4$)-alkylaminocarbonyl in the context of the invention represents an amino group, which is linked via a carbonyl group and which contains a straight-chain or branched or two identical or different straight-chain or branched alkyl substituents in each case having 1 to 4 carbon atoms. Examples which may be mentioned are: methylaminocarbonyl, dimethylaminocarbonyl, diethylaminocarbonyl, n-propyl-aminocarbonyl, isopropylmethylaminocarbonyl, tert-butylaminocarbonyl and tert-butyl-methylaminocarbonyl. A mono- or dialkylaminocarbonyl radical is preferred whose straight-chain or branched alkyl radical or whose identical or different straight-chain or branched alkyl radicals contain 1 to 3 carbon atoms.

$(C_3–C_8)$-cycloalkyl or $(C_3–C_6)$-cycloalkyl in the context of the invention represents a cycloalkyl radical having 3 to 8 or 3 to 6 carbon atoms. Examples which may be mentioned are: cyclopropyl, cyclobutyl, cyclopentyl, cyclohexyl or cyclooctyl. Cyclopropyl, cyclopentyl and cyclohexyl are preferred.

$(C_1–C_{18})$-alkyl, $(C_1–C_6)$-alkyl or $(C_1–C_4)$-alkyl whose carbon chain is optionally interrupted by an an oxygen or sulfur atom or by a radical $NR^7$ in the context of the invention represents a straight-chain or branched alkyl radical having 1 to 8, 1 to 6 or 1 to 4 carbon atoms, whose carbon chain contains an oxygen or sulfur atom or a radical $NR^7$ as a further chain member. A straight-chain or branched alkyl radical having 1 to 6 carbon atoms is preferred, whose carbon chain contains an oxygen or sulfur atom or a radical $NR^7$ as a further chain member. A straight-chain or branched alkyl radical having 1 to 4 carbon atoms is particularly preferred, whose carbon chain contains an oxygen atom as a further chain member.

$(C_3–C_8)$-cycloalkyl or $(C_4–C_6)$-cycloalkyl whose carbon chain is optionally interrupted by an oxygen or sulfur atom or by a radical $NR^{10}$ in the context of the invention represents a cycloalkyl radical having 3 to 8 or 4 to 6 carbon atoms, whose carbon chain contains an oxygen or sulfur atom or a radical $NR^{10}$ as a further ring member. A cycloalkyl radical having 4 to 6 carbon atoms is preferred, whose carbon chain contains an oxygen or sulfur atom or a radical $NR^{10}$ as a further ring member. A cycloalkyl radical having 4 to 6 carbon atoms is particularly preferred, whose carbon chain contains an oxygen atom or a radical $NR^{10}$ as a further ring member.

The saturated or partially unsaturated 3- to 10-membered, mono- or bicyclic heterocycle in the context of the invention represents a monocyclic or bicyclic ring having 3 to 10 ring atoms, which is bound by a nitrogen atom to the adjacent carbonyl/thiocarbonyl group and contains up to two further heteroatoms and optionally one or more double or triple bonds. In the case of the bicycle, the two rings can be linked in spirocyclic form, or the bridgehead atoms of the two rings are directly adjacent or are separated by means of one to a plurality of ring atoms. Examples which may be mentioned are aziridin-1-yl, azetidin-1-yl, pyrrolidin-1-yl, pyrrolin-1-yl, piperidin-1-yl, 1,2,5,6-tetrahydropyridin-1-yl, morpholin-4-yl, thiomorpholin-4-yl, hexa-hydroazepin-1-yl, 2,3 -dihydro-(1H)-indol-1-yl, octahydroindol-1-yl, 8-aza-bicyclo-[3.2.1]octan-8-yl, 3-aza-bicyclo[3.2.1]octan-3-yl, 3-aza-bicyclo[3.2.0]heptan-3-yl, 3,8-diaza-1-oxa-bicyclo[4.3.0]nonan-8-yl, azacyclodecen-1-yl. Azetidin-1-yl, pyrrolidin-1-yl, 3-aza-bicyclo[3.2.0]heptan-3-yl and morpholin-4-yl are preferred.

Physiologically acceptable salts of the compounds according to the invention can be salts of the substances according to the invention with mineral acids, carboxylic acids or sulfonic acids. Particularly preferred salts are, for example, those with hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, propionic acid, lactic acid, tartaric acid, citric acid, fumaric acid, maleic acid or benzoic acid.

Depending on the substitution pattern, the compounds according to the invention can exist in stereoisomeric forms, which behave either as image and mirror image (enantiomers), or which do not behave as image and mirror image (diastereomers). The invention relates both to the enantiomers and diastereomers, and to their respective mixtures. Just like the diastereomers, the racemic forms can be separated in a known manner into the stereoisomerically uniform constituents.

Preferred compounds of the general formula (I) are those in which $R^1$ and $R^2$ are identical or different and independently of one another represent hydrogen, fluorine, chlorine, bromine, $(C_1–C_4)$-alkyl, $(C_1–C_4)$-alkoxy, trifluoromethyl, trifluoromethoxy or a radical —$NR^5R^6$, in which $R^5$ and $R^6$ are identical or different and represent hydrogen, $(C_1–C_3)$-alkyl, $(C_1–C_3)$-acyl, $(C_1–C_4)$-alkoxycarbonyl, carbamoyl, mono- or di-$(C_1–C_3)$-alkylaminocarbonyl, $R^3$ and $R^4$ are identical or different and independently of one another represent $(C_1–C_6)$-alkyl whose carbon chain is optionally interrupted by an oxygen or sulfur atom or by a radical $NR^7$ and which is optionally mono- or polysubstituted by radicals selected from the group consisting of $(C_3–C_6)$-cycloalkyl, $(C_1–C_4)$-alkoxy, hydroxyl, fluorine, chlorine or $NR^8R^9$, represent $(C_4–C_6)$-cycloalkyl whose carbon chain is optionally interrupted by an oxygen or sulfur atom or by a radical $NR^{10}$ and which is optionally mono- or polysubstituted by radicals selected from the group consisting of $(C_1–C_4)$-alkoxy, hydroxyl, fluorine, chlorine or $NR^{11}R^{12}$, in which $R^7$, $R^8$, $R^9$, $R^{10}$, $R^{11}$ and $R^{12}$ are identical or different and independently of one another denote hydrogen, $(C_1–C_3)$-alkyl, $(C_1–C_3)$-acyl, $(C_1–C_4)$-alkoxycarbonyl, carbamoyl, mono- or di-$(C_1–C_3)$-alkylaminocarbonyl, or $R^3$ and $R^4$, together with the nitrogen atom, form a saturated or partially unsaturated 3- to 9-membered, mono- or bicyclic heterocycle, which optionally contains up to two further heteroatoms selected from the group consisting of nitrogen, oxygen or sulfur, and which is optionally substituted by radicals selected from the group consisting of $(C_1–C_3)$-alkyl, $(C_1–C_3)$-alkoxy, hydroxyl, fluorine, $COOR^{13}$or $NR^{14}R^{15}$, in which $R^{13}$ denotes hydrogen, methyl or ethyl, and $R^{14}$ and $R^{15}$ are identical or different and independently of one another denote hydrogen, $(C_1–C_3)$-alkyl, $(C_1–C_3)$-acyl, $(C_1–C_4)$-alkoxycarbonyl, carbamoyl, mono- or di-$(C_1–C_3)$-alkylaminocarbonyl, and X represents oxygen or sulfur, and their salts.

Particularly preferred compounds of the general formula (I) are those in which $R^1$ and $R^2$ are identical or different and independently of one another represent hydrogen, fluorine, chlorine, methyl, ethyl, methoxy, ethoxy, trifluoromethyl, trifluoromethoxy or a radical —$NR^5R^6$, in which $R^5$ and $R^6$ are identical or different and represent hydrogen, methyl, formyl, acetyl or methoxycarbonyl, $R^3$ and $R^4$ are identical or different and independently of one another represent $(C_1-C_4)$-alkyl whose carbon chain is optionally interrupted by an oxygen atom and which is optionally mono- or polysubstituted by radicals selected from the group consisting of hydroxyl, methoxy, fluorine, chlorine or $NR^8R^9$, represent $(C_4-C_6)$-cycloalkyl whose carbon chain is optionally interrupted by an oxygen atom or by a radical $NR^{10}$ and which is optionally mono- or polysubstituted by radicals selected from the group consisting of hydroxyl, methoxy, fluorine, chlorine or $NR^{11}R^{12}$, in which $R^7, R^8, R^9, R^{10}, R^{11}$ and $R^{12}$ are identical or different and independently of one another denote hydrogen, methyl, formyl, acetyl or methoxycarbonyl, or $R^3$ and $R^4$, together with the nitrogen atom, form a saturated or partially unsaturated 4- to 9-membered, mono- or bicyclic heterocycle, which optionally contains up to two further heteroatoms selected from the group consisting of nitrogen, oxygen or sulfur, and which is optionally substituted by radicals selected from the group consisting of methyl, methoxy, hydroxyl, fluorine or $NR^{14}R^{15}$, in which $R^{14}$ and $R^{15}$ are identical or different and independently of one another denote hydrogen, methyl, formyl, acetyl or methoxycarbonyl, and X represents oxygen, and their salts.

Very particularly preferred compounds of the general formula (I) are those in which $R^1$ and $R^2$ are identical or different and independently of one another represent hydrogen, fluorine, chlorine, methyl, methoxy, trifluoromethyl, trifluoromethoxy or amino, $R^3$ and $R^4$ are identical or different and independently of one another represent methyl or ethyl, which is optionally substituted by chlorine, or $R^3$ and $R^4$, together with the nitrogen atom, form an azetidin-1-yl, pyrrolidin-1-yl, morpholin-4-yl or 3-azabicyclo[3.2.0]heptan-3-yl radical, and X represents oxygen, and their salts.

Moreover, processes for the preparation of compounds of the general formula (I) have been found, characterized in that compounds of the general formula (II),

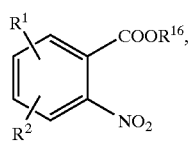

(II)

in which $R^1$ and $R^2$ have the meaning indicated above and $R^{16}$ represents methyl or ethyl, are reacted with a reductant, optionally in the presence of an acid and optionally in an inert solvent, to give compounds of the general formula (III)

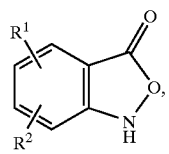

(III)

in which $R^1$ and $R^2$ have the meaning indicated above, and

[A] subsequently reacted with a compound of the general formula (IV),

(IV), in which

X represents oxygen or sulfur, and q denotes 1, 2 or 3, optionally in the presence of an inert solvent and of a base, to give compounds of the general formula (V)

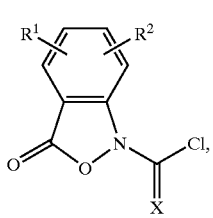

(V)

in which $R^1$, $R^2$ and X have the meaning indicated above, which are finally reacted with a compound of the general formula (VI),

(VI), in which $R^3$ and $R^4$ have the meaning indicated above, optionally in the presence of an auxiliary base, to give compounds of the general formula (I).

Alternatively, compounds of the general formula (I) can also be obtained by a process in which

[B] firstly, a compound of the general formula (VI) is optionally reacted in the presence of an inert solvent and of a base with a compound of the general formula (IV) to give compounds of the general formula (VII)

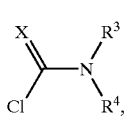

(VII)

in which $R^3$, $R^4$ and X have the meaning indicated above, which are then reacted with a compound of the general formula (III), optionally in the presence of an auxiliary base, to give compounds of the general formula (I).

Suitable solvents for the processes are customary organic solvents which do not change under the reaction conditions.

These include ethers such as diethyl ether, dioxane, tetrahydrofuran, glycol dimethyl ether, or hydrocarbons such as benzene, toluene, xylene, hexane, cyclohexane or petroleum fractions, or halogenohydrocarbons such as dichloromethane, trichloromethane, tetrachloromethane, dichloroethylene, trichloroethylene or chlorobenzene, or ethyl acetate, pyridine, dimethyl sulfoxide, N,N-dimethylformamide, hexamethylphosphoramide, acetonitrile, acetone or nitromethane. Likewise, it is possible to use mixtures of the solvents mentioned. For the process (II)→(III), water or a mixture of water with one of the organic solvents mentioned is also suitable. A mixture of diethyl ether and water is preferred for this process. For the processes (III)→(V) and (V)→(I), dichloromethane and trichloromethane are preferred. Dichloromethane is particularly preferred.

Reductants which can be employed for the process (II)→(III) are, for example, zinc, hydrogen in the presence of a catalyst, or hydrazine in the presence of a catalyst such as Raney nickel or palladium. Suitable catalysts for the reduction with hydrogen are transition metals such as, for example, palladium, platinum or rhodium, preferably palladium. Zinc is preferred for the process (II)→(III).

Suitable acids for the process (II)→(III) are, for example, acetic acid or ammonium chloride. Ammonium chloride is preferred.

Bases which can be employed for the process according to the invention are in general inorganic or organic bases. These preferably include alkali metal hydroxides such as, for example, sodium hydroxide or potassium hydroxide, alkaline earth metal hydroxides such as, for example, barium hydroxide, alkali metal carbonates such as sodium carbonate, potassium carbonate or cesium carbonate, alkaline earth metal carbonates such as calcium carbonate, or alkali metal or alkaline earth metal alkoxides such as sodium methoxide or potassium methoxide, sodium ethoxide or potassium ethoxide or potassium tert-butoxide, or organic amines ($(C_1-C_6)$-trialkylamines) such as triethylamine, or heterocycles such as 1,4-diazabicyclo[2.2.2]octane (DABCO), 1,8-diazabicyclo[5.4.0]undec-7-ene (DBU), pyridine, N,N-dimethylaminopyridine, methylpiperidine or morpholine. Triethylamine is preferred for the process (V)→(I).

In general, the base is employed in an amount from 0.05 mol to 10 mol, preferably from 1 mol to 3 mol, relative to 1 mol of the compound of the formula (V).

The processes according to the invention are in general carried out in a temperature range from −20° C. to +100° C., preferably from 0° C. to +60° C.

The processes according to the invention are in general carried out at normal pressure. However, it is also possible to carry out the processes at elevated pressure or at slightly reduced pressure (e.g. in a range from 0.5 to 5 bar).

The compounds of the general formulae (II), (IV) and (VI) are known or can be prepared according to customary methods.

Surprisingly, the new compounds show an unforeseeable, valuable spectrum of pharmacological action.

They are distinguished as highly effective inhibitors of acylpeptide hydrolase (ACPH). They can be employed on their own or in combination with other medicaments for the prophylaxis and/or treatment of disorders of the central nervous system. Examples which may be mentioned are cognitive disorders such as Alzheimer's disease and other forms of dementia, and also depression, schizophrenia and anxiety. They are also suitable for the prophylaxis and control of the sequelae of cerebral infarcts (cerebral apoplexy) such as stroke and cerebral ischemias. Likewise, the compounds according to the invention can be employed for the treatment of craniocerebral trauma and for the control of states of pain.

Their use for the treatment of cognitive disorders, in particular of Alzheimer's disease or other forms of dementia, is preferred.

Their use for the treatment of cerebral infarcts, craniocerebral trauma and pain is likewise preferred.

In vitro determination of the Inhibition of ACPH

In the standard experiment, rat brains are homogenized in a 10-fold volume (w/v) of 50 mM tris HCl buffer, 1 mM EDTA, 100 mM NaCl, 0.1% BSA, 1 mM DDT, pH 7.2. The protein concentration of the homogenate is adjusted to approximately 5 mg/ml by dilution with buffer. The incubation batch (110 μl) contains 40 μl of buffer, various test concentrations of the test substances to be tested in 10 μl of buffer, 50 μl of brain homogenate and 100 μM N-acetyl-methionyl-aminomethyl-coumarin as the enzyme substrate. Before addition of the substrate, the reaction mixture is preincubated at room temperature for 30 min. The enzyme reaction is started by substrate addition. The reaction time is 30 min. Afterwards, the samples are activated in a fluorimeter at 390 nm and determined quantitatively at 460 nm. The $IC_{50}$ value is calculated from the enzyme activity in the presence of increasing concentrations of test substance in the test. For the measurement of the ACPH activity, purified enzyme from liver or other organs can also be used and also homogenates of other organs having ACPH activity, such as liver or erythrocytes.

The results are shown by way of example for some compounds in Table 1 below:

TABLE 1

| Example No. | $IC_{50}$ [nM] |
| --- | --- |
| 4 | 6 |
| 5 | 18 |
| 6 | 48 |
| 7 | 99 |

The efficacy of the substances identified in this way in the treatment and prevention of cognitive disorders is confirmed with the aid of known standard animal models for learning and memory (cf., for example, 'Alzheimer's Disease: Biology, Diagnosis and Therapeutics', Iqbal et al., ed.; 1997, John Wiley, pp. 781–786). Suitable animals for this are, for example, passive or active avoidance behavior, classical or operant conditioning, spatial orientation tests, or object or subject recognition tests. A particularly suitable model which is recommended is the 'Morris test', which is based on the spatial memory (J. Neurosci. Methods 1984, 11, 47–60).

Morris Test:

Using the Morris test, spatial orientation learning in rodents is determined. The test is outstandingly suitable for the assessment of the learning- and memory-promoting action of substances. In this test, rats or mice are trained to locate a platform which is not visible to them as the only possibility of escape from a water-filled swimming pool. A proven method is to train the animals four times per day over the period of 5 days. The test substances are in this case administered daily during the experiment at a defined time, e.g. 30 min before the first swimming experiment per day. Controls receive the corresponding vehicle. The learning power of the animals is expressed in a training-related reduction of the distance swum between the starting position and platform, and in a reduction of the swimming time until reaching the platform, i.e. the better the animal recognizes the location of the platform, the shorter is the distance covered and the more rapidly the platform is readied. The test is carried out using cognitively impaired animals, such as old animals or animals having experimentally induced brain damage.

Rats with a lesion of the entorhinal cortex are an animal model of AlzheiTner's disease. The bilateral lesion of the entorhinal cortex is produced by the intracerebral injection of the excitotoxin ibotenic acid. It leads to a severe impairment of the learning power in the Morris test.

The new active compounds can be converted in a known manner into the customary formulations, such as tablets, coated tablets, pills, granules, aerosols, syrups, emulsions, suspensions and solutions, using inert, nontoxic, pharmaceutically suitable vehicles or solvents. In this connection, the therapeutically active compound should in each case be present in a concentration of approximately 0.0001 to 90% by weight, preferably 0.0001 to 1.0% by weight, of the total mixture, i.e. in amounts which are sufficient in order to achieve the dosage range indicated.

The formulations are produced, for example, by extending the active compounds using solvents and/or vehicles, optionally using emulsifiers and/or dispersing agents, where, for example, if water is used as a diluent, organic solvents can optionally be used as auxiliary solvents.

Administration is carried out in a customary manner, preferably orally, transdermally or parenterally, in particular perlingually or intravenously.

In general, it has proven advantageous in the case of intravenous administration to administer amounts of approximately 0.00001 to 10 mg/kg, preferably approximately 0.0001 to 1 mg/kg of body weight, to achieve efficacious results.

In spite of this, it may optionally be necessary to depart from the amounts mentioned, namely depending on the body weight or the type of administration route, on the individual behavior toward the medicament, the manner of its formulation and the time or interval at which administration takes place. Thus in some cases it may be sufficient to manage with less than the abovementioned minimum amount, while in other cases the upper limit mentioned has to be exceeded.

In the case or the administration of relatively large amounts, it may be advisable to divide these into a number of individual doses over the course of the day.

Abbreviations:

| EI | electron impact ionization |
| DCI | direct chemical ionization |
| LCMS | liquid chromatography-coupled mass spectroscopy |

STARTING COMPOUNDS

Example I

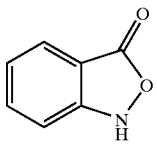

60 g (331 mmol) of methyl 2-nitrobenzoate are introduced into 600 ml of diethyl ether and 840 ml of water with stirring. The mixture is then treated with 35.97 g (672 mmol) of ammonium chloride. Zinc (90.1 g, 1.378 mol) is then added over the course of 5 min to the 2-phase mixture thus obtained. The mixture is stirred at room temperature for 20 min, and the undissolved zinc is filtered off and washed with ether. The aqueous phase is separated off and extracted twice with diethyl ether. The combined ether phases are extracted with 1 N NaOH solution until this remains colorless. The combined NaOH phases are adjusted to pH 6 using 1 N HCl. An amorphous solid precipitates in the course of this. The solid is filtered off with suction, taken up in methylene chloride, and the solution is dried over sodium sulfate and concentrated.

Yield: 46.7 g (77.8% of theory); MS (DCI): 153 (M+NH$_4^+$: 100%); $^1$H-NMR (DMSO, TMS): δ 11.85 (br, 1H), 7.7–7.88 (m, 2H), 7.2–7.4 (m, 2H).

All compounds shown in Table 2 were synthesized analogously to the procedure of Example I.

TABLE 2

| Ex. No. | Structure | Yield in % | M.p. in °C. | R$_f$ (cyclohexane/ ethyl acetate 1:1) | MS |
|---|---|---|---|---|---|
| II | 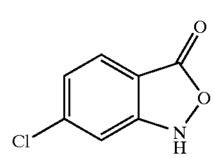 | 56 | 158 (dec.) | 0.45 | 169 [M$^+$, 100%] EI |
| III | 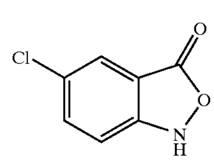 | 32 | 126 (dec.) | 0.39 | 169 [M$^+$, 100%] EI |

TABLE 2-continued

| Ex. No. | Structure | Yield in % | M.p. in °C. | R_f (cyclohexane/ ethyl acetate 1:1) | MS |
|---|---|---|---|---|---|
| IV | 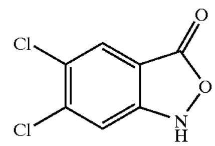 | 24 | >200 (dec.) | 0.40 | 249 [M$^+$, 100%] EI |
| V | 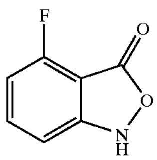 | 26 | 158 | 0.32 | 171 [M + NH$_4^+$, 100%] DCI |
| VI | 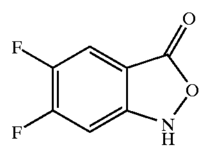 | 56 | 131 | 0.43 | 171 [M$^+$, 100%] EI |
| VII | 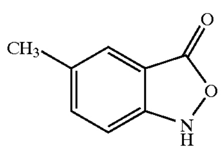 | 7 | 169 | 0.32 | 150 [M + H$^+$, 40%] LCMS |

PREPARATION EXAMPLES

Example 1

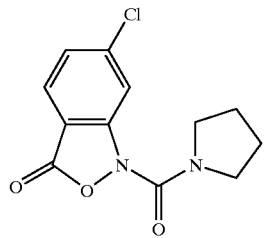

A solution of 200 mg (1.18 mmol) of compound from Example II and 457 mg (3.54 mmol) of ethyldiisopropylamine in 2.5 ml of methylene chloride is introduced at RT with stirring and treated with 165 mg (81.24 mmol) of 1-pyrrolidinecarbonyl chloride (J. Am. Chem. Soc. 1951, 73, 1214). After stirring at room temperature for 16 hours, the mixture is hydrolyzed using water, extracted with ether, washed with saturated NaCl solution, dried over sodium sulfate and concentrated. Chromatography on silica gel using petroleum ether to ethyl acetate 4:1 yields the product.

Yield: 227 mg (72% of theory); MS (DCI): 283 [M+NH$_4^+$: 100%]; $^1$H-NMR (DMSO, TMS): δ 7.95 (d, J=8 Hz, 1H), 7.78 (d, J=2 Hz), 7.48 (dd, J=8 Hz, J=2 Hz, 1H), 3.55–3.7 (m, 4H), 1.85–1.95 (m, 2H).

The example compounds shown in Table 3 were prepared in an analogous manner:

TABLE 3

| Ex. No. | Structure | M.p. in °C. | R_f (cyclohexane/ethyl acetate 1:1) |
|---|---|---|---|
| 1 | 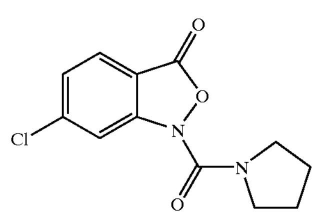 | 98 | 0.49 |

TABLE 3-continued

| Ex. No. | Structure | M.p. in ° C. | R$_f$ (cyclohexane/ethyl acetate 1:1) |
| --- | --- | --- | --- |
| 2 | 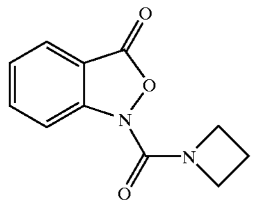 | 163 | 0.31 |
| 3 | 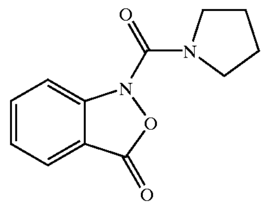 | 99 | 0.38 |
| 4 | 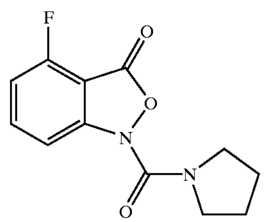 | 109 | 0.34 |
| 5 | 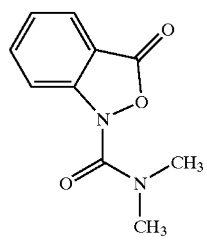 | 93 | 0.34 |
| 6 | 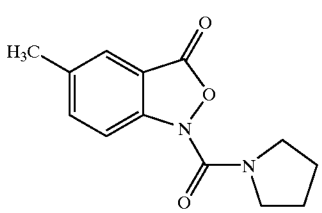 | 129 | 0.45 |
| 7 | 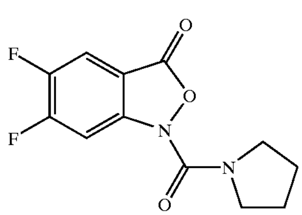 | 133 | 0.45 |
| 8 | 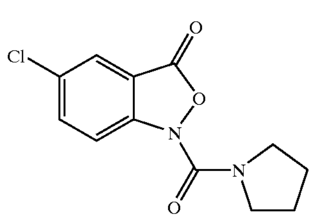 | 103 | 0.45 |

TABLE 3-continued
| Ex. No. | Structure | M.p. in °C. | $R_f$ (cyclohexane/ethyl acetate 1:1) |
|---|---|---|---|
| 9 | 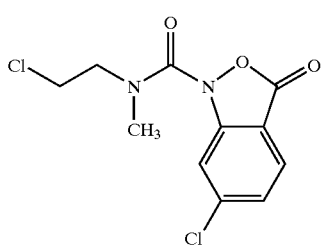 | liquid | 0.50 |
| 10 | 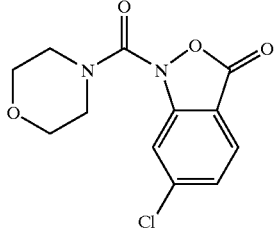 | 116 | 0.43 |
| 11 | 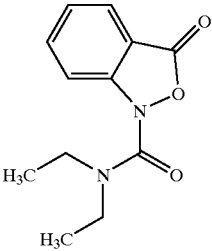 | — | 0.50 |
| 12 | 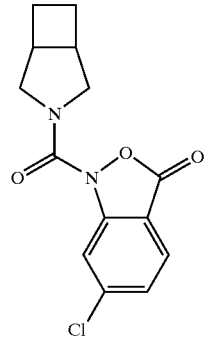 | 98 | 0.59 |
| 13 | 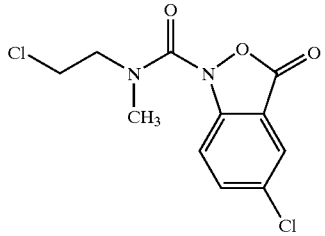 | 52 | 0.47 |

TABLE 3-continued

| Ex. No. | Structure | M.p. in ° C. | $R_f$ (cyclohexane/ethyl acetate 1:1) |
|---|---|---|---|
| 14 | 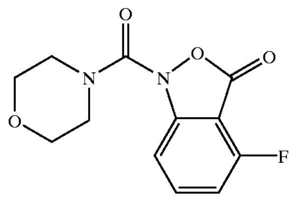 | 141 | 0.24 |
| 15 | 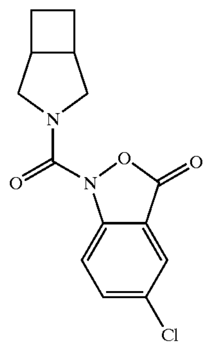 | 85 | 0.57 |
| 16 | 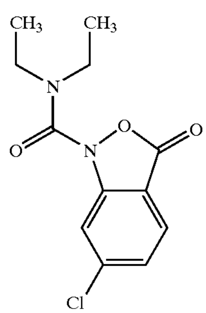 | — | 0.59 |
| 17 | 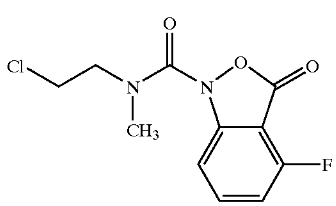 | liquid | 0.36 |
| 18 | 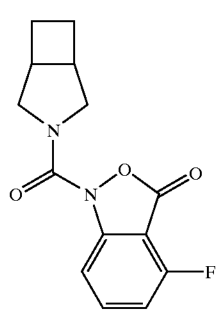 | | 0.47 |

TABLE 3-continued

| Ex. No. | Structure | M.p. in °C. | $R_f$ (cyclohexane/ethyl acetate 1:1) |
|---|---|---|---|
| 19 | 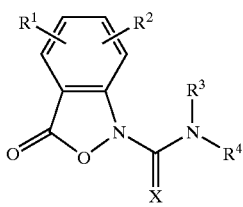 | 153 | 0.33 |

What is claimed is:

1. A compound of the general formula (I), $$\text{(I)}$$

in which
R¹ and R² are identical or different and independently of one another
represent hydrogen, halogen, $(C_1-C_6)$-alkyl, $(C_1-C_6)$-alkoxy, $(C_1-C_3)$-perfluoroalkyl, $(C_1-C_3)$-perfluoroalkoxy or a radical $—NR^5R^6$,
in which
R⁵ and R⁶ are identical or different and represent hydrogen, $(C_1-C_4)$-alkyl, $(C_1-C_4)$-acyl, $(C_1-C_4)$-alkoxycarbonyl, carbamoyl, mono- or di-$(C_1-C_4)$-alkylaminocarbonyl,
R³ and R⁴ are identical or different and independently of one another
represent $(C_1-C_8)$-alkyl whose carbon chain is optionally interrupted by an oxygen or sulfur atom or by a radical $NR^7$ and which is optionally mono- or polysubstituted by radicals selected from the group consisting of $(C_3-C_6)$-cycloalkyl, $(C_1-C_4)$-alkoxy, hydroxyl, halogen or $NR^8R^9$,
represent $(C_3-C_8)$-cycloalkyl whose carbon chain is optionally interrupted by an oxygen or sulfur atom or by a radical $NR^{10}$ and which is optionally mono- or polysubstituted by radicals selected from the group consisting of $(C_1-C_4)$-alkoxy, hydroxyl, halogen or $NR^{11}R^{12}$,
in which
$R^7, R^8, R^9, R^{10}, R^{11}$ and $R^{12}$ are identical or different and independently of one another have the meaning mentioned for R⁵,
or
R³ and R⁴, together with the nitrogen atom, form a saturated or partially unsaturated 3- to 10-membered, mono- or bicyclic heterocycle, which optionally contains up to two further heteroatoms selected from the group consisting of nitrogen, oxygen or sulfur, and which is optionally substituted by radicals selected from the group consisting of $(C_1-C_4)$-alkyl, $(C_1-C_4)$-alkoxy, hydroxyl, halogen, $COOR^{13}$ or $NR^{14}R^{15}$,
in which
$R^{13}$ denotes hydrogen or $(C_1-C_4)$-alkyl, and
$R^{14}$ and $R^{15}$ are identical or different and independently of one another have the meaning mentioned for R⁵,
and
X represents oxygen or sulfur,
and its salts.

2. A compound as claimed in claim 1, where
R¹ and R² are identical or different and independently of one another
represent hydrogen, fluorine, chlorine, bromine, $(C_1-C_4)$-alkyl, $(C_1-C_4)$-alkoxy, trifluoromethyl, trifluoromethoxy or a radical $—NR^5R^6$,
in which
R⁵ and R⁶ are identical or different and represent hydrogen, $(C_1-C_3)$-alkyl, $(C_1-C_3)$-acyl, $(C_1-C_4)$-alkoxycarbonyl, carbamoyl, mono- or di-$(C_1-C_3)$-alkylaminocarbonyl,
R³ and R⁴ are identical or different and independently of one another
represent $(C_1-C_6)$-alkyl whose carbon chain is optionally interrupted by an oxygen or sulfur atom or by a radical $NR^7$ and which is optionally mono- or polysubstituted by radicals selected from the group consisting of $(C_3-C_6)$-cycloalkyl, $(C_1-C_4)$-alkoxy, hydroxyl, fluorine, chlorine or $NR^8R^9$,
represent $(C_4-C_6)$-cycloalkyl whose carbon chain is optionally interrupted by an oxygen or sulfur atom or by a radical $NR^{10}$ and which is optionally mono- or polysubstituted by radicals selected from the group consisting of $(C_1-C_4)$-alkoxy, hydroxyl, fluorine, chlorine or $NR^{11}R^{12}$,
in which
$R^7, R^8, R^9, R^{10}, R^{11}$ and $R^{12}$ are identical or different and independently of one another denote hydrogen, $(C_1-C_3)$-alkyl, $(C_1-C_3)$-acyl, $(C_1-C_4)$-alkoxycarbonyl, carbamoyl, mono- or di-$(C_1-C_3)$-alkylaminocarbonyl,
or
R³ and R⁴, together with the nitrogen atom, form a saturated or partially unsaturated 3- to 9-membered, mono- or bicyclic heterocycle, which optionally contains up to two further heteroatoms selected from the group consisting of nitrogen, oxygen or sulfur, and which is optionally substituted by radicals selected from the group consisting of $(C_1-C_3)$-alkyl, $(C_1-C_3)$-alkoxy, hydroxyl, fluorine, $COOR^{13}$ or $NR^{14}R^{15}$,
in which
$R^{13}$ denotes hydrogen, methyl or ethyl, and
$R^{14}$ and $R^{15}$ are identical or different and independently of one another denote hydrogen, $(C_1-C_3)$-alkyl, $(C_1-C_3)$-acyl, $(C_1-C_4)$-alkoxy-carbonyl, carbamoyl, mono- or di-$(C_1-C_3)$-alkylaminocarbonyl,
and
X represents oxygen or sulfur,
and its salts.

3. A compound as claimed in claim 1, where
$R^1$ and $R^2$ are identical or different and independently of one another represent hydrogen, fluorine, chlorine, methyl, ethyl, methoxy, ethoxy, trifluoromethyl, trifluoromethoxy or a radical $NR^5R^6$,
in which
$R^5$ and $R^6$ are identical or different and represent hydrogen, methyl, formyl, acetyl or methoxycarbonyl,
$R^3$ and $R^4$ are identical or different and independently of one another
represent $(C_1-C_4)$-alkyl whose carbon chain is optionally interrupted by an oxygen atom and which is optionally mono- or polysubstituted by radicals selected from the group consisting of hydroxyl, methoxy, fluorine, chlorine or $NR^8R^9$,
represent $(C_4-C_6)$-cycloalkyl whose carbon chain is optionally interrupted by an oxygen atom or by a radical $NR^{10}$ and which is optionally mono- or polysubstituted by radicals selected from the group consisting of hydroxyl, methoxy, fluorine, chlorine or $NR^{11}R^{12}$,
in which
$R^7$, $R^8$, $R^9$, $R^{10}$, $R^{11}$ and $R^{12}$ are identical or different and independently of one another denote hydrogen, methyl, formyl, acetyl or methoxycarbonyl,
or
$R^3$ and $R^4$, together with the nitrogen atom, form a saturated or partially unsaturated 4- to 9-membered, mono- or bicyclic heterocycle, which optionally contains up to two further heteroatoms selected from the group consisting of nitrogen, oxygen or sulfur, and which is optionally substituted by radicals selected from the group consisting of methyl, methoxy, hydroxyl, fluorine or $NR^{14}R^{15}$,
in which
$R^{14}$ and $R^{15}$ are identical or different and independently of one another denote hydrogen, methyl, formyl, acetyl or methoxycarbonyl,
and
X represents oxygen,
and its salts.

4. A compound as claimed in claim 1, where
$R^1$ and $R^2$ are identical or different and independently of one another
represent hydrogen, fluorine, chlorine, methyl, methoxy, trifluoromethyl, trifluoromethoxy or amino,
$R^3$ and $R^4$ are identical or different and independently of one another represent methyl or ethyl, which is optionally substituted by chlorine,
or
$R^3$ and $R^4$, together with the nitrogen atom, form an azetidin-1-yl, pyrrolidin-1-yl, morpholin-4-yl or 3-azabicyclo[3.2.0]heptan-3-yl radical,
and
X represents oxygen,
and its salts.

5. A process for the preparation of compounds of the general formula (I) as claimed in claim 1, characterized in that compounds of the general formula (II),

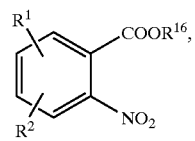

(II)

in which
$R^1$ and $R^2$ have the meaning indicated in claim 1 and $R^{16}$ represents methyl or ethyl,
are reacted with a reductant, optionally in the presence of an acid and optionally in an inert solvent, to give compounds of the general formula (III)

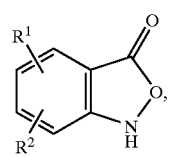

(III)

in which
$R^1$ and $R^2$ have the meaning indicated in claim 1,
and
[A] subsequently reacted with a compound of the general formula (IV),

$(Cl_2C{=}X)_q$ (IV), in which
X represents oxygen or sulfur, and
q denotes 1, 2 or 3,
optionally in the presence of an inert solvent and of a base, to give compounds of the general formula (V)

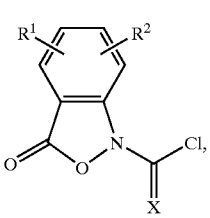

(V)

in which
$R^1$, $R^2$ and X and the meaning indicated in claim 1, which are finally reacted with a compound of the general formula (VI)

$HNR^3R^4$ (VI), in which
$R^3$ and $R^4$ have the meaning indicated in claim 1,
optionally in the presence of an auxiliary base, to give compounds of the general formula (I),
or
[B] firstly, a compound of the general formula (VI) is optionally reacted in the presence of an inert solvent and of a base with a compound of the general formula (IV) to give compounds of the general formula (VII)

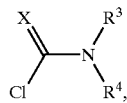 (VII)

in which

R³, R⁴ and X have the meaning indicated in claim 1, which are then reacted with a compound of the general formula (III), optionally in the presence of an auxiliary base, to give compounds of the general formula (I).

6. A pharmaceutical composition comprising a compound as claimed in any one of claims 1 to 4.

7. A method for the treatment of disorders of the central nervous system comprising administering to a subject in need thereof an effective amount of a compound as claimed in any one of claims 1 to 4.

8. A method for the treatment of cognitive disorders comprising administering to a subject in need thereof an effective amount of a compound as claimed in any one of claims 1 to 4.

9. A method for the treatment of cerebral infarcts, craniocerebral trauma and pain comprising administering to a subject in need thereof an effective amount of a compound as claimed in any one of claims 1 to 4.

10. The method of claim 9, wherein said cognitive disorder is selected from the group consisting of Alzheimer's disease and other forms of dementia.

* * * * *